United States Patent [19]

Spillman, Jr.

[11] Patent Number: 5,677,489

[45] Date of Patent: Oct. 14, 1997

[54] DISTRIBUTED STRUCTURAL CHARACTERISTIC DETECTION SYSTEM USING A UNIDIRECTIONAL ACOUSTIC WAVEGUIDE

[75] Inventor: William Bert Spillman, Jr., Charlotte, Vt.

[73] Assignee: Simmonds Precision Products, Inc., Richfield, Ohio

[21] Appl. No.: 484,038

[22] Filed: Jun. 7, 1995

Related U.S. Application Data

[63] Continuation of Ser. No. 93,413, Jul. 19, 1993, abandoned.

[51] Int. Cl.$^6$ .................................................. G01N 29/04
[52] U.S. Cl. .............................. 73/598; 73/624; 73/644
[58] Field of Search ............................... 73/598, 600, 624, 73/627, 644, 602, 599

[56] References Cited

U.S. PATENT DOCUMENTS

| | | | |
|---|---|---|---|
| 3,910,105 | 10/1975 | Hoffstedt | 73/88 A |
| 4,158,169 | 6/1979 | Harrold et al. | 324/52 |
| 4,312,562 | 1/1982 | Segawa et al. | 350/96.15 |
| 4,329,876 | 5/1982 | Chen et al. | 73/618 |
| 4,352,038 | 9/1982 | Moreton | 310/323 |
| 4,461,178 | 7/1984 | Chamuel | 73/599 |
| 4,481,821 | 11/1984 | Chamuel | 73/617 |
| 4,586,381 | 5/1986 | Chamuel | 73/643 |
| 4,590,803 | 5/1986 | Harrold | 73/590 |
| 4,654,520 | 3/1987 | Griffiths | 250/227 |
| 4,669,814 | 6/1987 | Dyott | 350/96.15 |
| 4,742,318 | 5/1988 | Jen et al. | 333/141 |
| 4,788,868 | 12/1988 | Wilk | 73/760 |
| 4,840,481 | 6/1989 | Spillman, Jr. | 356/32 |
| 4,863,270 | 9/1989 | Spillman, Jr. | 356/345 |
| 4,894,806 | 1/1990 | Jen et al. | 367/7 |
| 5,024,092 | 6/1991 | Harrold et al. | 73/602 |
| 5,052,227 | 10/1991 | Le Floc'h et al. | 73/644 |

FOREIGN PATENT DOCUMENTS

| | | |
|---|---|---|
| 6148758 | 3/1986 | Japan. |
| 1171377 | 11/1969 | United Kingdom. |

OTHER PUBLICATIONS

Copy of European Search Report for European Application No. 94305306 6 dated Sep. 13, 1995.

Chen et al., "New Grating Acoustic Scanner," Ultrasonics Symposium, Sep. 25–27, 1978, Cherry Hill, New Jersey, pp. 775–779.

*Primary Examiner*—Ian J. Lobo
*Attorney, Agent, or Firm*—Richard A. Romanchik; Leonard L. Lewis

[57] ABSTRACT

Apparatus for acoustically analyzing a structure having distributed characteristics comprising a first acoustic waveguide for transmitting an acoustic signal through a portion of the structure, a second acoustic waveguide for receiving a reflected acoustic signature of the structure and transmitting the acoustic signature to a sensor; the sensor producing an output that corresponds to the acoustic signature. The apparatus and methods are particularly adaptable to detecting distributed structural characteristics.

28 Claims, 2 Drawing Sheets

DISTRIBUTED STRUCTURAL CHARACTERISTIC DETECTION SYSTEM USING A UNIDIRECTIONAL ACOUSTIC WAVEGUIDE

This is a continuation of application Ser. No. 08/093,413 filed on Jul. 19, 1993 now abandoned.

BACKGROUND OF THE INVENTION

The invention relates generally to apparatus and methods for structural analysis, and more particularly to structural analysis apparatus and methods that use acoustic signals for detecting structural characteristics.

The use of acoustic energy to detect surface flaws in structures is well known. Acoustic energy transmitted through the structure towards a sensor or target is reflected at defect sites, thereby reducing the amount of acoustic energy that is transmitted to the sensor. Time domain analysis can also be used to determine the approximate location of the defect with respect to the acoustic source and sensor.

Structural damage or irregularities or other characteristics can be detected due to the fact that such characteristics are manifested as a non-homogeneous region that will at least partially reflect acoustic waves. For example, U.S. Pat. No. 4,586,381 illustrates an ultrasonic transducer which has respective ends of a source waveguide and a sensor waveguide placed in contact with a structure to be analyzed. The presence of a defect in the structure between the two waveguides is apparent as a variation in the amplitude of the sensor output signal. U.S. Pat. No. 4,481,821 discloses an electro-elastic crack detector which uses a magnetostrictive delay line arranged parallel to a current carrying line. The presence of a crack in the surface being inspected produces transverse eddy currents which magnetostrictively induce acoustic pulses in the delay line which are detected by an ultrasonic sensor coupled to the end of the delay line to indicate the location of the crack.

Although such devices can detect structural defects by use of waveguides in proximity to the structure, various aspects of the known systems present design limitations restrict applications, particularly to complex structures such as aircraft. For example, the use of eddy currents for detecting defects may be unsuitable in some applications and difficult to interpret the return signals. Also, having a system wherein only the ends of waveguides are used for detecting defects does not easily permit detection for distributed structural analysis. In many applications, defects other than on the surface of the structure need to be detected.

The need exists, therefore, for apparatus and methods for structural analysis that can conveniently use acoustic energy for detecting structural characteristics, especially for performing distributed structural analysis.

SUMMARY OF THE INVENTION

In view of the aforementioned disadvantages and problems, the invention contemplates, in one embodiment, apparatus for acoustically analyzing a structure comprising first acoustic waveguide means for transmitting an acoustic signal through a portion of the structure; second acoustic waveguide means for receiving a reflected acoustic signature from the structure and transmitting the acoustic signature to a sensor; the sensor producing an output that corresponds to the acoustic signature.

The invention also contemplates the methods embodied in the operation and use of such apparatus, as well as a method of detecting faults in a structure comprising the steps of:

sending an acoustic pulse through a source waveguide proximate a surface of a structure so that at least a portion of the acoustic pulse goes into a portion of the structure, using a unidirectional acoustic waveguide disposed adjacent and parallel the source waveguide to absorb at least a portion of the acoustic pulse transmitted through the structure portion and, receiving a portion of the acoustic pulse absorbed by the unidirectional waveguide by a sensor that converts the unidirectional waveguide acoustic signal to an output that corresponds to magnitude and distance of acoustic energy received by said unidirectional waveguide.

These and other aspects and advantages of the invention will be readily understood and appreciated by those skilled in the art from the following detailed description of the preferred embodiments as the best mode contemplated for carrying out the invention, in view of the accompanying drawings.

DETAILED DESCRIPTION OF THE INVENTION

Figure 1:
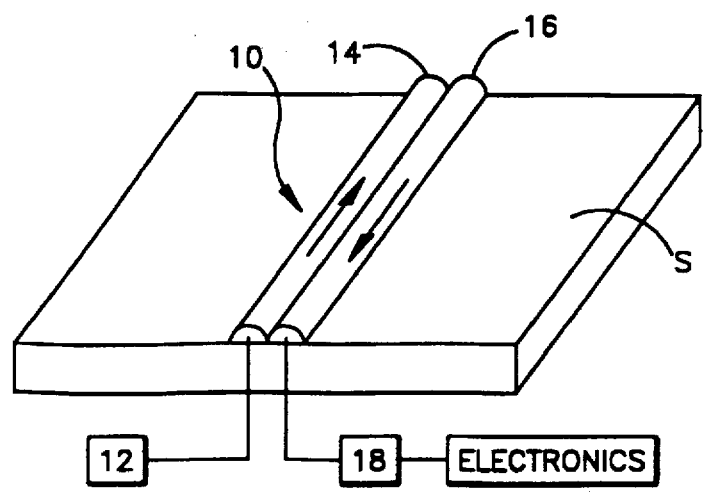
FIG. 1 is a simplified schematic in perspective of an acoustic distributed structural analyzer according to the invention disposed on the surface of a structure to be analyzed.

With reference to FIG. 1, there is illustrated a portion of a structure "S" with a distributed acoustic analyzer, indicated generally at 10, disposed on the surface of the structure. Although the invention is described herein as using surface mounted waveguides, those skilled in the art will readily appreciate that in other applications the waveguides could be embedded in the structure. For example, embedded waveguides could be used with structures made of carbon composite materials.

An acoustic energy source 12 is coupled to one end of an elongate acoustic source waveguide 14 to transmit acoustic pulses in the direction of the arrow along the waveguide. The source waveguide is acoustically coupled to the structure such as with an acoustic gel or other adhesive that provides a good acoustic impedance matched interface between the waveguide and the structure. Although exact impedance matching is not required, it is preferred for many applications that the acoustic impedance of the waveguide be closely matched to the acoustic impedance of the structure. The waveguide is generally in the form of an elongated solid. The waveguide may be hollow or in any geometric form. Additionally, the transmission medium within the waveguide may be a contained liquid or gaseous material. The waveguide, preferably is tuned in shape and density to the frequency of the sound wave that is to be carried. Such tuning allows for the optimal transmission of sound energy within the waveguide. The acoustic source 12 can be, for example, an ultrasonic transducer or other suitable device that emits acoustic energy into the source waveguide.

Adjacent and aligned generally parallel to the acoustic source waveguide 14 is an elongate unidirectional waveguide 16, coupled to an acoustic sensor 18. The unidirectional waveguide is also preferably closely matched to the acoustic impedance of the structure, and can be disposed on or embedded in the structure by any convenient means, similar to the source waveguide. However, as will be described in greater detail hereinafter, the unidirectional waveguide is constructed so as to transmit acoustic energy in a single direction that is opposite the direction acoustic energy travels along the source waveguide.

Acoustic waves generated by the source 12 are directed into the acoustic source waveguide 14. Because of the impedance match between the waveguides and the structure, the acoustic energy of the transmitted pulses "leaks" into the structure S.

Figure 2:
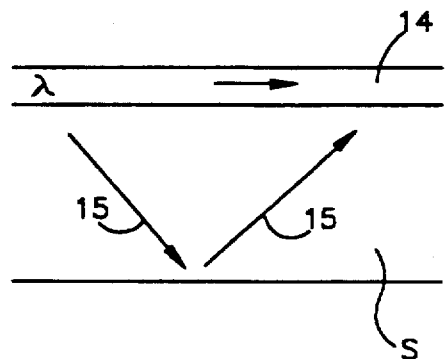
FIG. 2 is a longitudinal cross-section view of the acoustic source waveguide and the structure to be analyzed shown in FIG. 1.

The "leaking" of acoustic energy from the acoustic source waveguide 14 into the structure S is illustrated in a representative manner in FIG. 2. The acoustic waves generated by the source 12 generally propagates down the source waveguide 14. Some of the acoustic energy passes into the structure S (due to impedance matching) as represented by the arrows 15. In the example of a relatively homogenous structure as depicted in FIG. 2, the acoustic energy is reflected at a structural boundary, B, of the structure back towards the waveguides. Some of this reflected energy, which energy can be referred to as an acoustic signature of the structure, passes into the unidirectional waveguide 16.

Figure 3:
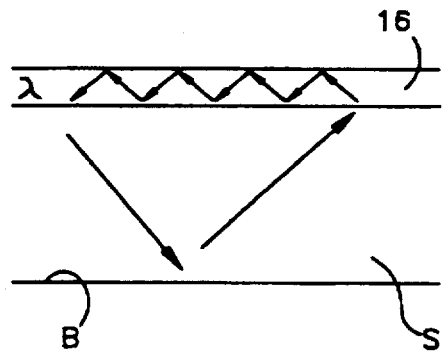
FIG. 3 is a longitudinal cross-section view of a unidirectional waveguide and the structure to be analyzed shown in FIG. 1.

The return of acoustic energy reflected by the structure S into the unidirectional waveguide 16 is illustrated in a representative manner in FIG. 3, with the arrows again indicating the direction of travel of the acoustic pulses. In order to provide a simple way to realize a time domain based distributed detection system, part of the reflected acoustic energy passes into the unidirectional waveguide 16 and is transmitted back towards the direction of the source 12. The reverse travel is preferred to assure that the acoustic signature received at the sensor 18 is a time domain based signal that corresponds to propagation of the acoustic energy through the structure in the region of the waveguides. This allows the location of irregularities or defects in the structure to be determined as a function of the round trip time for the acoustic signals to return to the sensor 18 (wherein the velocity of the acoustic waves through the waveguides and structure will be a known or determinable quantity).

Figure 4:
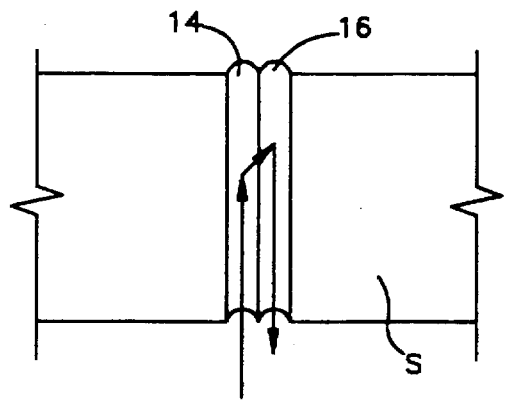
FIG. 4 is a top plan view of an acoustic source waveguide and an unidirectional waveguide arranged adjacent and parallel on the surface of a structure to be analyzed.

FIG. 4 illustrates a plan view of the manner in which a portion of the acoustic pulses sent into the acoustic source waveguide 14 crosses over during reflection through the structure S into the unidirectional waveguide 16 to be transmitted back to the sensor 18. Although the use of a unidirectional waveguide to transmit the acoustic signature in a direction opposite the source waveguide direction is the preferred teaching, those skilled in the art will appreciate that other configurations are possible that would produce a suitable time domain acoustic signature.

Figure 5:
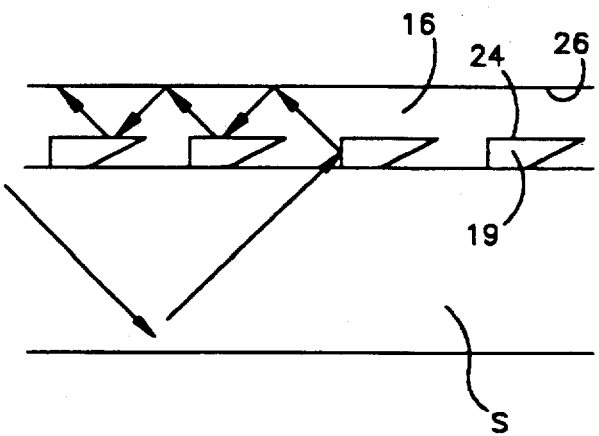
FIG. 5 is a more detailed schematic in longitudinal cross-section of a unidirectional waveguide suitable for use with the present invention.

FIG. 5 illustrates in cross-section one embodiment of a unidirectional waveguide 16, showing an internal structure which results in wave transmission in a substantially single direction. Air gaps or voids 19 are defined by internal walls 20, including a vertical portion 22 and a horizontal portion 24, to provide a vertical reflective surface which reflects incoming acoustic waves towards the top internal edge 26 of the waveguide 16, and a horizontal reflective surface to repeat the reflective pattern in the direction of the arrows. The voids or air gaps 19 present a substantial acoustic impedance mismatch such that most of the acoustic energy that impinges on the interface wall 22 is reflected in a desired direction along the unidirectional waveguide. Those skilled in the art will readily appreciate that there are many different ways to provide an impedance mismatch or other suitable means for accomplishing a reversing unidirectional waveguide.

The sensor 18 may be any conveniently available acoustic transducer that converts acoustic energy to a suitable output such as, for example, electrical signals. The sensor 18 output can be analyzed by appropriate electronics to determine the characteristics of the structure based, for example, on the magnitude and time delays of various signal pulses in the acoustic signature. Thus, location and severity of an irregularity or defect in the structure can be determined, for example, by comparing the return signature with a known signature for a homogenous (defect free) structure.

The electronics (not shown) can be conventional in design for detecting peak amplitudes and time delay characteristics of the acoustic signature. The electronics can further include memory devices for storing data corresponding to a reference signature, all under the control of a device or circuit such as a microprocessor or other suitable device.

Figure 6:
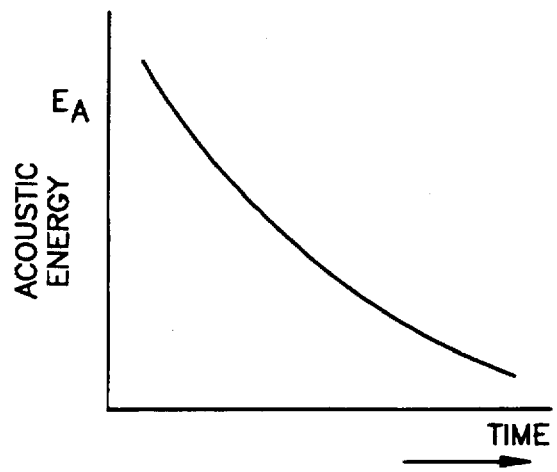
FIG. 6 is a representative plot for purposes of illustrating acoustic energy versus time for energy transmitted through a regular structure.

Operation of the described embodiment of an apparatus in accordance with the invention is as follows. Assuming a homogenous structure, acoustic energy propagates along the source waveguide 14. Part of this acoustic energy passes through the structure in the region of the waveguides and then into the unidirectional waveguide. The unidirectional waveguide reflects the acoustic energy back towards the sensor 18 in a direction generally opposite the source waveguide propagation. As shown in FIG. 6, the received acoustic signature is typically characterized by a smooth generally exponential decay of acoustic energy E over time for a generally homogeneous structure. This is because the intensity of the acoustic energy dissipates as it travels down the source waveguide 14. Such a pattern can be used as a reference or calibration for later monitoring of the same or similar structures.

Figure 7:
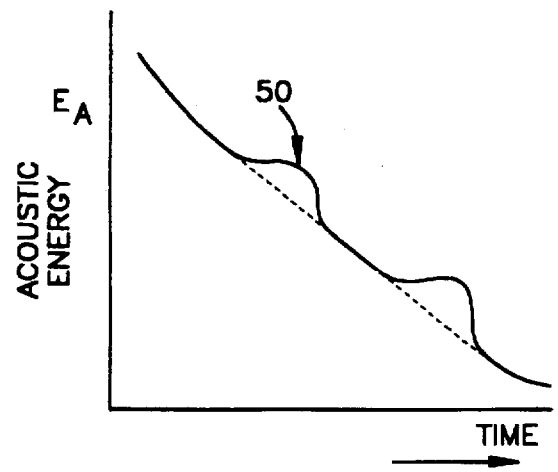
FIG. 7 is a representative plot for purposes of illustrating acoustic energy versus time for energy transmitted through an irregular structure.
Figure 8:
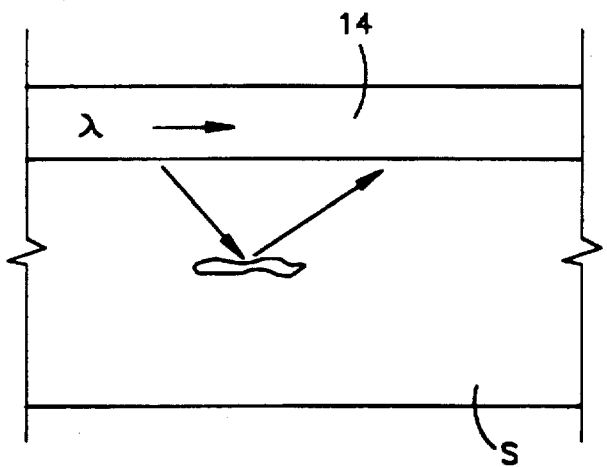
FIG. 8 is a longitudinal cross-section view of an acoustic source waveguide mounted on the surface of a structure containing a defect.

However, when the structure contains distributed defects or irregularities, these anomalies produce different reflection patterns in the acoustic signature. FIG. 7 graphically illustrates in a representative manner the acoustic energy signature that travels along the unidirectional waveguide 16 in the case where the acoustic energy has passed through damaged or nonhomogeneous areas in the structure, resulting in perturbations of the return signal. For example, a defect such as a crack or void produces an impedance mismatch at an interface in the structure. This interface reflects the acoustic energy back to the unidirectional waveguide 16 to produce a perturbation in the acoustic signature that differs (such as at 50) from the reference signature (FIG. 6). The position of the defect in the structure with respect to the unidirection waveguide 16 causes the perturbation 50 to be detected at a particular point in time during the return transmission or reflection. Since the velocity of the acoustic energy through the waveguides and structure is a determinable quantity, then the distance of the defect that caused the perturbation 50 along the length of the waveguide can be determined. It should be noted that in FIG. 5, the spacing between the interfaces 22 is somewhat exaggerated for clarity and understanding. The actual spacing can be selected by the designer based on the degree of accuracy desired for determining positions of defects and irregularities in the structure. FIG. 8 illustrates the manner in which an acoustic pulse leaked into the structure S from acoustic source waveguide 14 is prematurely reflected back towards the unidirectional waveguide by the presence of a crack or any other physical incongruity which reflects acoustic energy to cause the perturbation in the return signal.

Thus, the invention provides apparatus and methods for structural analysis of distributed characteristics of the structure using acoustic energy. A significant advantage of the invention is that it provides an inexpensive acoustic detection system for distributed structural analysis. For example, the waveguides can be low cost plastic waveguides, with the acoustic source and sensor made of PVDF polyvinyldifluoride materials. The acoustic elements of the apparatus can be disposed on the structure with any suitable adhesive such as epoxy that permits good acoustic coupling between the waveguides and the structure. The apparatus is especially convenient for assembly with the structure at the same time that the structure is formed. For example, in the case of structures made from composite materials, the acoustic elements can be securely applied to the structure when the structural member is laid up in a mold or cured, or at any other convenient process step.

While the invention has been shown and described with respect to specific embodiments thereof, this is for the purpose of illustration rather than limitation, and other variations and modifications of the specific embodiments herein shown and described will be apparent to those skilled in the art within the intended spirit and scope of the invention as set forth in the appended claims.

I claim:

1. An acoustic analyzer comprising, an elongated acoustic source waveguide coupled to an acoustic energy source and acoustically coupled along a first lengthwise portion to a structure to be analyzed, an elongated unidirectional waveguide acoustically coupled along a second lengthwise portion to the structure and generally parallel to said acoustic source waveguide, said unidirectional waveguide being constructed to have a substantially single direction for transmitting acoustic energy, and sensor means coupled to an end of said unidirectional waveguide to detect acoustic energy transmitted into said unidirectional waveguide along said second lengthwise portion from said source waveguide along said first lengthwise portion.

2. The acoustic analyzer of claim 1 wherein said acoustic source waveguide and said unidirectional waveguide are elongate elements and are disposed parallel to each other on a common surface of the structure to be analyzed.

3. The acoustic analyzer of claim 1 wherein said unidirectional waveguide is positioned adjacent said acoustic source waveguide.

4. The acoustic analyzer of claim 1 wherein said acoustic source and said sensor are positioned at the same respective ends of said acoustic source waveguide and said unidirectional waveguide.

5. The analyzer of claim 1 wherein said acoustic source waveguide and said unidirectional waveguide are attached to the structure to be analyzed.

6. The acoustic analyzer of claim 1 wherein said sensor is an acoustic transducer.

7. The acoustic analyzer of claim 6 wherein said transducer is connected to circuit means for producing an output that corresponds to magnitude and reflection distance of acoustic energy incident upon said sensor.

8. The acoustic analyzer of claim 1 wherein acoustic energy is transmitted from said acoustic source, through said source waveguide and into a portion of the structure.

9. The acoustic analyzer of claim 8 wherein a portion of said acoustic energy transmitted into the structure is reflected to said unidirectional waveguide to provide an acoustic signature of the structure.

10. The acoustic analyzer of claim 9 wherein said unidirectional waveguide comprises means for reflecting acoustic energy in a direction opposite a direction said acoustic energy is transmitted through said source waveguide.

11. The acoustic waveguide of claim 10 wherein said waveguides are made of material having an acoustic impedance similar to the acoustic impedance of the structure.

12. The acoustic waveguide of claim 11 wherein said reflecting means of said unidirectional waveguide comprise air interfaces in said waveguide that cause acoustic reflections towards a predetermined direction.

13. A method of detecting faults in a structure comprising the steps of:

sending an acoustic pulse through an elongated source waveguide acoustically coupled along a first length thereof to a surface of the structure so that acoustic energy goes into a portion of the structure along said first length, using an elongated unidirectional acoustic waveguide having a substantially single direction for transmitting acoustic energy and acoustically coupled along a second length thereof to the structure to receive along said second length at least a portion of said acoustic energy transmitted into said structure portion and, producing an output related to magnitude and distance of acoustic energy received by said unidirectional waveguide.

14. The method of claim 13 wherein the step of processing includes timing the interval between transmission of a pulse into said source waveguide and receipt of a reflection of the pulse through said unidirectional waveguide.

15. The method of claim 13 wherein said processing of said acoustic pulse received through said unidirectional waveguide includes comparing the dissipation of acoustic energy over time with the dissipation of acoustic energy for a structure of a known condition.

16. Apparatus for acoustically analyzing a structure comprising a first acoustic waveguide means acoustically coupled lengthwise to the structure for transmitting acoustic energy along a first length thereof through a portion of the structure; second acoustic waveguide means acoustically coupled lengthwise to the structure for receiving along a second length thereof an acoustic signature of the structure based on said acoustic energy transmitted along said first length of said first waveguide means into the structure and then into said second waveguide means along said second length; said second acoustic waveguide means being a unidirectional waveguide constructed to have a substantially single direction for transmitting acoustic energy; and a sensor for producing an output based on said acoustic signature.

17. The apparatus of claim 16 wherein said first and second waveguide means are disposed generally lengthwise parallel to each other and are acoustically coupled to the structure.

18. The apparatus of claim 17 wherein said first and second waveguide means are disposed on a common surface of the structure such that at least a portion of acoustic energy transmitted from said first waveguide means along its length into the structure is received by said second acoustic waveguide means.

19. The apparatus of claim 18 wherein said unidirectional waveguide transmits acoustic energy in a direction substantially opposite direction of transmitting acoustic energy through said first acoustic waveguide means.

20. The apparatus of claim 19 wherein said sensor output can be input to means for comparing said acoustic signature to a reference acoustic signature for determining location and magnitude of distributed structural irregularities.

21. The apparatus of claim 16 wherein said waveguide means are acoustically coupled to the structure substantially along their entire lengths.

22. The apparatus of claim 16 wherein acoustic energy leaks from said first waveguide means into the structure and returns to the sensor along the second waveguide means.

23. The apparatus of claim 22 wherein acoustic energy leaks into the structure along a length of said first waveguide means such that the acoustic signature represents a time domain based signal of distributed features of the structure over said length.

24. The apparatus of claim 23 wherein the acoustic energy is transmitted as pulses.

25. The analyzer of claim 1 wherein said unidirectional waveguide transmits acoustic energy in a substantially single direction.

26. The analyzer of claim 1 wherein said unidirectional waveguide comprises means for transmitting acoustic energy in a substantially single direction.

27. The analyzer of claim 1 further comprising control means for detecting time and amplitude characteristics of said acoustic energy received by said sensor means from said unidirectional waveguide relative to time and amplitude of acoustic energy applied to said acoustic source waveguide from said acoustic source, said detected acoustic energy representing an acoustic signature of the structure.

28. The analyzer of claim 27 wherein said control means comprises memory means for storing a reference acoustic signature, and means for comparing said reference acoustic signature with a detected acoustic signature.

* * * * *